United States Patent [19]

Danna

[11] Patent Number: 5,734,418
[45] Date of Patent: Mar. 31, 1998

[54] ENDOSCOPE WITH TAB IMAGER PACKAGE

[75] Inventor: Dominck Danna, Syracuse, N.Y.

[73] Assignee: Welch Allyn, Inc., Skaneateles Falls, N.Y.

[21] Appl. No.: 682,370

[22] Filed: Jul. 17, 1996

[51] Int. Cl.⁶ .............. A62B 1/04; H04N 7/18; H04N 9/47; A61B 1/04
[52] U.S. Cl. .............. 348/76; 348/65; 348/68; 348/87; 600/109; 600/110
[58] Field of Search .............. 348/65, 68, 76, 348/87; 257/727, 731; 600/109, 110, 112; 29/840; A61B 1/04; A62B 1/04; H04N 7/18, 9/47

[56] References Cited

U.S. PATENT DOCUMENTS

| | | | |
|---|---|---|---|
| 4,573,450 | 3/1986 | Arakawa. | |
| 4,622,954 | 11/1986 | Arakawa et al. | |
| 4,646,723 | 3/1987 | Arakawa | 600/110 |
| 4,682,219 | 7/1987 | Arakawa. | |
| 4,692,608 | 9/1987 | Cooper et al. | |
| 4,720,178 | 1/1988 | Nishioka et al. | 600/109 |
| 4,809,680 | 3/1989 | Yabe | 600/109 |
| 4,890,159 | 12/1989 | Ogiu | 348/72 |
| 4,918,521 | 4/1990 | Yabe et al. | |
| 4,998,971 | 3/1991 | Fukunishi | 600/110 |
| 5,040,069 | 8/1991 | Matsumoto et al. | 348/76 |
| 5,220,198 | 6/1993 | Tsuji | 348/75 |
| 5,418,566 | 5/1995 | Kameishi | 348/65 |
| 5,427,087 | 6/1995 | Ito et al. | 600/110 |
| 5,479,694 | 1/1996 | Baldwin | 29/840 |
| 5,541,367 | 7/1996 | Swamy | 29/840 |
| 5,566,441 | 10/1996 | Marsh et al. | 29/840 |

*Primary Examiner*—Tommy P. Chin
*Assistant Examiner*—Nhon T. Diep
*Attorney, Agent, or Firm*—Wall Marjama & Bilinski

[57] ABSTRACT

An endoscope including an insertion tube containing a TAB imager package in the distal end thereof. The imager is mounted in a complementary opening formed in a circuit board and the board is aligned along the central axis of the insertion tube. Fine pitch leads extend from between the imager and a transparent window covering the imager to both sides of the imager. The leads are bonded to traces on the board which connect the leads to circuitry mounted on the board. A reflecting surface optically couples the imager to a forward viewing lens system.

9 Claims, 2 Drawing Sheets

ENDOSCOPE WITH TAB IMAGER PACKAGE

BACKGROUND OF THE INVENTION

This invention relates to an endoscope, and in particular, to a compact imager assembly for use in the distal end of an insertion tube of a video endoscope.

The increased availability of solid state imagers based on CCD and CMOS technologies has surpassed the ability of conventional wire bonding techniques to take full advantage of the space saving features afforded by these small devices. An advanced integrated circuit technology known as tape automated bonding (TAB) has been developed which permits fine pitch lead patterns to be bonded to small size electronic components such as a CCD imager. A TAB imager package typically consists of a solid state imager over which is placed a transparent window. Fine pitch imager leads extend outwardly to either side of the imager from between the imager and the window.

TAB packages are traditionally relatively weak in a structural sense and require some further structural support to provide additional strength to the device. The additional structural support, however, generally adds to the size of the overall package. Accordingly, the package cannot be effectively utilized in confined spaces such as the viewing head of a video endoscope.

U.S. Pat. No. 4,692,608 to Cooper et al. describes a compact imager system for use in an endoscope. In this arrangement, a CCD imager is mounted along the central axis of the insertion tube and is optically coupled to a forward viewing lens system by means of a reflecting prism. A second CCD imager is used as a register to store image data derived by the first imager and is mounted adjacent to the first imager in co-planar relation therewith. A circuit board is mounted in parallel alignment over the back side of the imager and contains circuitry for controlling the CCD imager and the CCD register and for transmitting data to and from a remote video processor. Both CCD devices are surrounded by an apron containing bonding pads and circuitry on the board is connected to the pad using conventional bonding techniques.

Although the Cooper et al. imager assembly takes advantage of the maximum area available in an insertion tube, the use of two side-by-side CCD devices and a circuit boarded stacked over the devices nevertheless consumes a good deal of valuable space in an environment where the savings of a few millimeters is extremely important.

SUMMARY OF THE INVENTION

It is therefore an object of the present invention to improve video endoscopes.

It is a further object of the present invention to reduce the size of the insertion tube of a video endoscope.

A still further object of the present invention is to provide a space-saving imager assembly for use in a video endoscope.

These and other objects of the present invention are attained by means of a video endoscope having an insertion tube containing a proximal end that is connected to a video processor and a distal end containing a TAB imager package. The TAB imager package includes a solid state imager and a transparent window mounted over the image recording surface of the imager. Fine pitch leads, which are bonded to the imager using the TAB process, extend outwardly from between the imager and the window to either side of the imager. The imager is contained within an opening formed in a circuit board so that the imager leads pass over the top surface of the board. The leads are bonded to traces on the board, which connect the imager to circuitry mounted on the board. The circuit board is mounted on the longitudinal axis of the insertion tube and the imager is optically coupled to forward viewing optics mounted in the distal end of the insertion tube by means of a reflecting prism.

BRIEF DESCRIPTION OF THE DRAWINGS

For a better understanding of these and other objects of the present invention, reference will be made to the following detailed description of the invention which is to be read in association with the accompanying drawings wherein.

DESCRIPTION OF THE INVENTION

Figure 1:
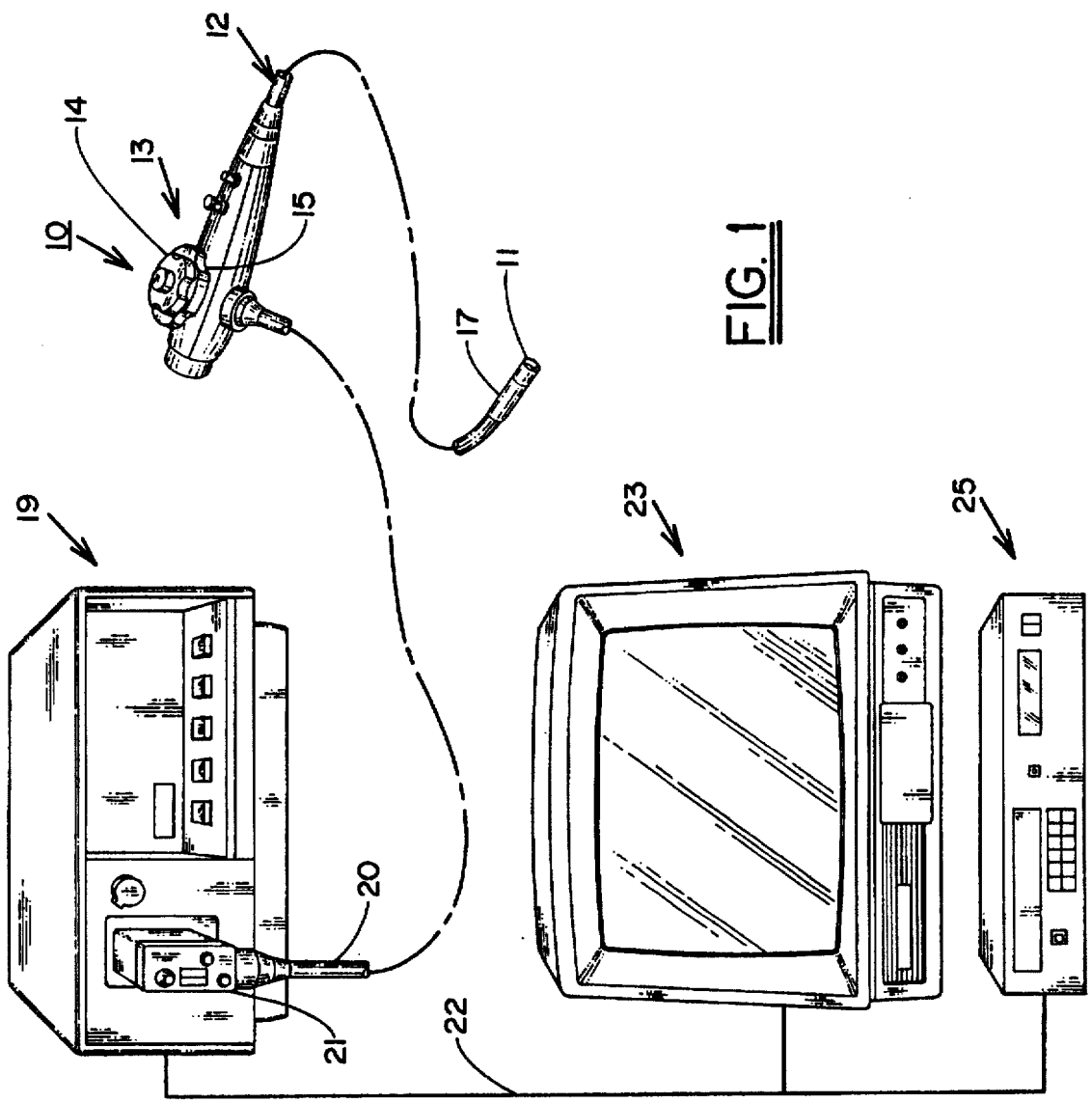
FIG. 1 is a perspective view of a video endoscope embodying the teachings of the present invention.

Turning initially to FIG. 1 there is illustrated a video endoscope generally referenced 10. As will be explained in greater detail below, a solid state imager assembly is mounted in the distal end 11 of the insertion tube 12 of the instrument. The proximal end of the insertion tube is connected to a control handle 13 that contains a pair of control knobs 14 and 15 the knobs are used to articulate the distal end of the insertion tube and permitting the insertion tube to be maneuvered through tight passages.

The control handle is connected to a plug-in module 21 by means of an umbilical chord 20. The module plugs into a video processor 19 whereby video related signals are exchanged between the processor and the imager assembly via transmission lines that pass through the umbilical chord and the insertion tube. A light source is also located in the processor which provides light conducted by a fiber bundle to the distal end of the insertion tube for illuminating a target located in the viewing range of the imager assembly. Video data from the processor is transmitted by means of line 22 to a video monitor 23 for display or can be passed on to a video recorder 25 for storage.

Figure 2:
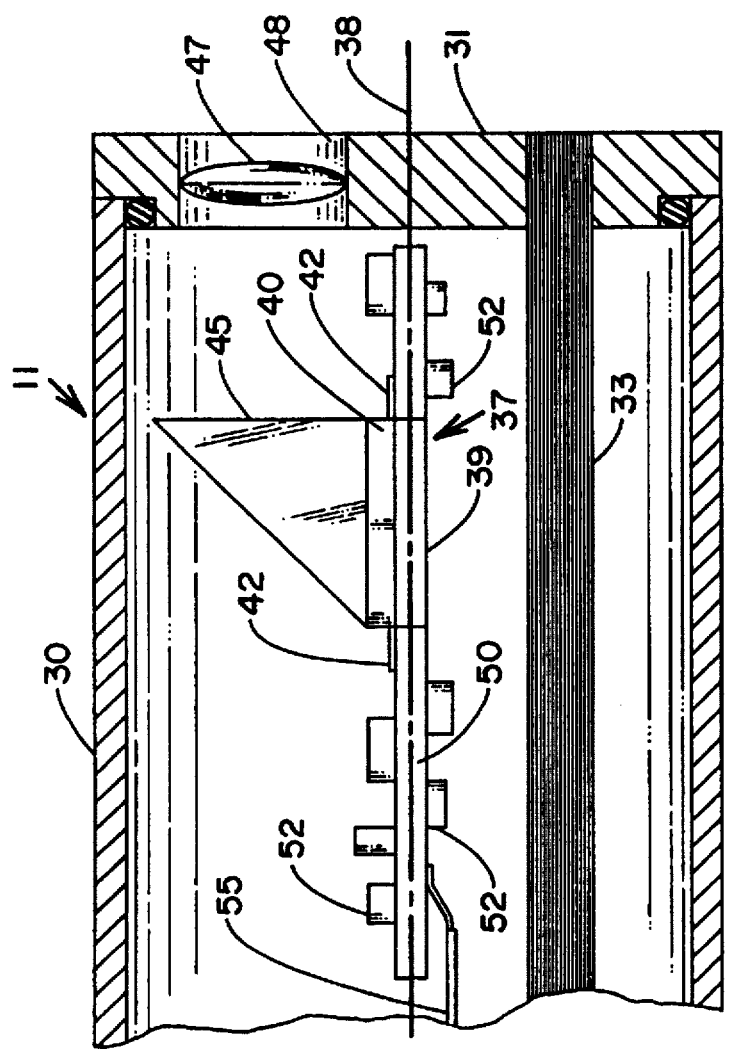
FIG. 2 is an enlarged side elevation of the imager assembly located in the distal end of the insertion tube of the video endoscope shown in FIG. 1.

Turning now to FIG. 2, there is shown an enlarged view of the distal end 11 of the insertion tube of the video endoscope 10. The distal end of the insertion tube includes a cylindrical housing 30 that is secured and sealed to the distal end face 31. A light carrying fiber bundle 33 passes through the insertion tube and is arranged to direct light into the target region of the instrument. Although not shown, other endoscopic related components may be passed through the insertion tube such as a biopsy channel, air and water lines and the like. Providing space within the confines of the insertion tube and, in particular, the distal end of the insertion tube which houses the video imager has been a long standing problem in the art. Any saving of space in this critical area, even if the saving is relatively small is extremely important if it leads to a reduction in the size (diameter) of the insertion tube.

In the present invention a TAB imager package 37 is mounted within the housing so that the solid state imager 39 lies along the central axis of the insertion tube. As noted above, the imager package includes the imager and a transparent window 40, preferably made of glass, which is mounted over the recording surface of the imager. Fine pitch leads 42—42 which are placed on the imager using the tape automatic bonding technique pass outwardly from between the imager and the window to either side of the imager. Spacing between the leads of 2 mm or less are attainable by this process.

The imager package 37 is mounted in a complementary opening formed in a circuit board 50 which is also mounted along the central axis of the housing. The imager is bonded to the side walls of the opening using an epoxy resin or the like. The thickness of the imager and the circuit board are about equal, each being approximately 0.020 inches thick.

With the imager bonded to the circuit board, the fine pitch leads extend outwardly over the top surface of the board and are bonded to suitable electric traces on the board. This, in turn, connects the leads to electric circuit components 52—52 mounted on both sides of the board. A series of transmission wires 55 are connected to the back of the board and pass through the insertion tube to the video processor 19 (FIG. 1) whereby signal and control related information is exchanged between the imager and the processor.

A prism 45 is bonded to the window of the imager package. The prism redirects a light image of a target from optical system 47 to the imager 39. The optical system is depicted as a single element mounted in a suitable opening 48 in the distal end face of the insertion tube, however, it should be clear that the optical system may include multiple elements capable of focussing an image of a target upon the recording surface of the solid state imager 39. In this particular embodiment, the prism is made of glass and is arranged to redirect the light image through an angle of 90°. A similar reflecting device such as a mirror, however, may be utilized without departing from the teachings of the present invention. The reflecting surface may also be set at various positions to redirect the light image at angles greater than or less than 90°.

While this invention has been explained with reference to the structure disclosed herein, it is not confined to the details set forth and this invention is intended to cover any modifications and changes as may come within the scope of the following claims:

What is claimed is:

1. An endoscope that includes an insertion tube having a distal end and a proximal end for connecting the insertion tube to a video processor, lens means mounted in the distal end of the insertion tube for focussing a target image upon a plane, means for redirecting said target image into a plane that is non-perpendicular with the axis of the lens means, a TAB imager package containing a solid state imager having an image recording surface mounted in said non-perpendicular plane, a transparent window having a shape substantially equal to that of the imager and being mounted over said image recording surface and fine pitched leads extending outwardly from opposing sides of said imager from between the imager and the window, a circuit board having a thickness about equal to that of said imager, said circuit board having an opening passing therethrough for containing said imager therein so that the imager leads pass along the top surface of said circuit board to both sides of imager, electrical circuitry mounted on at least one side of said board, and traces on said board for connecting said leads to said circuitry.

2. The endoscope of claim 1 wherein said circuitry is mounted upon both sides of said circuit board.

3. The endoscope of claim 1 wherein said means to redirect said target image is a prism.

4. The endoscope of claim 3 wherein one surface of said prism is bonded to the window of the imager package.

5. The endoscope of claim 1 wherein the pitch between said imager leads is about 2 mm or less.

6. The endoscope of claim 1 wherein said circuit board is positioned along the central axis of said insertion tube.

7. The endoscope of claim 1 wherein said imager and said board both are of equal thickness.

8. The endoscope of claim 7 wherein the imager and the board are about 0.020 inches thick.

9. The endoscope of claim 1 that further includes bonding means for bonding the imager to said board.

\* \* \* \* \*